United States Patent [19]

Schmerling

[11] 4,112,235

[45] Sep. 5, 1978

[54] TRANSESTERIFICATION OF CARBOXYLIC ACIDS

[75] Inventor: Louis Schmerling, Riverside, Ill.

[73] Assignee: UOP Inc., Des Plaines, Ill.

[21] Appl. No.: 736,648

[22] Filed: Oct. 28, 1976

[51] Int. Cl.$^2$ .............................................. C07C 67/10
[52] U.S. Cl. .............................. 560/1; 260/410.9 R;
260/410.9 N; 560/80; 560/95; 560/100;
560/105; 560/106; 560/122; 560/193; 560/201;
560/217; 560/234
[58] Field of Search ............... 260/491, 476 R, 468 R,
260/410.9 R, 410.9 N

[56] References Cited

U.S. PATENT DOCUMENTS

| 1,691,425 | 11/1928 | Ayres | 260/493 |
| 2,931,819 | 4/1960 | Mayne | 260/476 R |
| 3,649,655 | 3/1972 | Selwitz | 260/491 |
| 3,714,234 | 1/1973 | White | 260/491 |

*Primary Examiner*—James O. Thomas, Jr.
*Assistant Examiner*—Michael L. Shippen
*Attorney, Agent, or Firm*—James R. Hoatson, Jr.; Raymond H. Nelson; William H. Page, II

[57] ABSTRACT

Carboxylic acids may be esterified by reaction with esters in the presence of a catalytic amount of a tin halide catalyst, the reaction being effected at temperatures ranging from about 0° to about 150° C.

9 Claims, No Drawings

TRANSESTERIFICATION OF CARBOXYLIC ACIDS

BACKGROUND OF THE INVENTION

Heretofore, it has been believed that effecting a reaction with compounds containing oxygen such as first stage oxygenated compounds including alcohols, second stage oxygenated products such as aldehydes or ketones, or third stage oxygenated compounds such as acids would require the presence of stoichiometric amounts of metal halides such as aluminum chloride. However, as will hereinafter be shown in greater detail, it has now been discovered that esters may be reacted with carboxylic acids in the presence of a catalytic amount, that is, less than a stoichiometric quantity based on the carboxylic acid, of a tin halide whereby the acid may be esterified. By being able to utilize only catalytic amounts of the tin halide, it is possible to prepare the desired compounds at a relatively low cost, and thus render the process more attractive from an economic standpoint.

This invention relates to a process for the esterification of carboxylic acids. More specifically, the invention is concerned with a process for the esterification of carboxylic acids whereby said acids are reacted with an ester in the presence of a tin halide.

As hereinbefore set forth, it has now been discovered that carboxylic acids may be esterified by treating the acid with an ester and a tin halide thereby effecting a transesterification reaction which results in the formation of an ester of the carboxylic acid. This transesterification reaction is important inasmuch as the reaction offers a means of obtaining esters which otherwise would have to be prepared in a difficult manner. Esters will find a wide variety of uses in the chemical field. For example, sec-butyl acetate is used as a solvent for nitrocellulose, lacquers, thinners, nail enamels, celluloid products, etc.; sec-heptyl formate is used in artificial fruit essances; sec-octyl acetate is used in perfumery and flavors; allyl caproate is also used in perfumery and flavors; vinyl acetate is used in polyvinyl acetate resins, in latex paints, adhesives, textile finishing, etc.; benzyl acetate is used as an essential ingredient of artificial jasmine and other flowery perfumes, as a solvent for cellulose acetate and nitrate, in oils, lacquers, polishes, etc.; benzyl formate is used as a solvent as well as in perfumery and flavors; benzyl succinate is used in organic syntheses, etc.

It is therefore an object of this invention to provide a transesterification process.

A further object of this invention is to provide a process for the esterification of carboxylic acids by treating the acids with an ester in the presence of a tin halide.

In one aspect an embodiment of this invention resides in a process for the transesterification of a carboxylic acid which comprises reacting said acid with an ester in the presence of a tin halide catalyst at reaction conditions, and recovering the resultant esterified carboxylic acid.

A specific embodiment of this invention is found in a process for the transesterification of a carboxylic acid which comprises reacting propionic acid with allyl acetate in the presence of anhydrous stannic chloride at a temperature in the range of from about 0° to about 150° C. and a pressure in the range of from about atmospheric to about 100 atmospheres and recovering the resultant allyl propionate.

Other objects and embodiments will be found in the following further detailed description of the present invention.

As hereinbefore set forth the present invention is concerned with a process for the esterification of carboxylic acids wherein a carboxylic acid of a type hereinafter set forth in greater detail is treated with an ester in the presence of a tin halide catalyst. The reaction is effected under conditions which will include an operating temperature in the range of from about 0° to about 150° C. and preferably in a range of from about 40° to about 100° C. In addition to operating within the aforementioned temperatures, the reaction is also effected at pressures which may range from 1 to about 100 atmospheres, said superatmospheric pressures being effected by employing a substantially inert gas such as nitrogen, argon, helium, etc., the amount of pressure which is employed being that which is sufficient to maintain a major portion of the reactants in the liquid phase.

Suitable carboxylic acids which may be employed in the reaction with the ester will include fatty acids containing from 1 to about 20 carbon atoms or more per molecule such as formic acid, acetic acid, propionic acid, butyric acid, valeric acid, caproic acid, oenanthylic acid, caprylic acid, pelargonic acid, capric acid, undecylic acid, lauric acid, tridecoic acid, myristic acid, pentadecanoic acid, palmitic acid, margaric acid, stearic acid, arachidic acid, etc.; cycloalkanecarboxylic acids in which there are from 5 to about 8 carbon atoms in the ring such as cyclopentanecarboxylic acid, cyclohexanecarboxylic acid, cycloheptanecarboxylic acid, cyclooctanecarboxylic acid; aromatic acids such as benzoic acid, phenylacetic acid, phenylpropionic acid, phenylbutyric acid, phenylvaleric acid, o-toluic acid, m-toluic acid, p-toluic acid, phthalic acid, isophthalic acid, terephthalic acid, etc.; naphthalenecarboxylic acids such as naphthalenecarboxylic acid, 2-methylnaphthalenecarboxylic acid, 4-methylnaphthalenecarboxylic acid, 1,2-naphthalenedicarboxylic acid, 1,4-naphthalenedicarboxylic acid, etc.; unsaturated monobasic acids such as acrylic acid, crotonic acid, isocrotonic acid, tiglic acid, angelic acid, senecioic acid, oleic acid, etc.; saturated dibasic acids such as oxalic acid, malonic acid, succinic acid, glutaric acid, adipic acid, pimelic acid, suberic acid, azelaic acid, sebacic acid, brassic acid, etc.; unsaturated dibasic acids such as maleic acid, etc. It is to be understood that the aforementioned carboxylic acids are only representative of the class of acids which may be employed, and that the present invention is not necessarily limited thereto.

Suitable esters which may be employed in the transesterification reaction of the present invention will include alkyl, cycloalkyl, unsaturated aliphatic, cycloaliphatic and aryl esters. Examples of the alkyl esters include methyl formate, ethyl formate, propyl formate, butyl formate, amyl formate, hexyl formate, heptyl formate, octyl formate, nonyl formate, decyl formate, methyl acetate, ethyl acetate, propyl acetate, butyl acetate, amyl acetate, hexyl acetate, heptyl acetate, octyl acetate, nonyl acetate, decyl acetate, methyl propionate, ethyl propionate, propyl propionate, butyl propionate, amyl propionate, hexyl propionate, heptyl propionate, octyl propionate, nonyl propionate, decyl propionate, methyl butyrate, ethyl butyrate, propyl butyrate, butyl butyrate, amyl butyrate, hexyl butyrate, heptyl butyrate, octyl butyrate, nonyl butyrate, decyl butyrate, etc.; cycloalkyl esters such as cyclopentyl formate, cyclohexyl formate, cycloheptyl formate, cyclooctyl formate, cyclopentyl acetate, cyclohexyl acetate, cycloheptyl acetate, cyclooctyl acetate, cyclopentyl propionate, cyclohexyl propionate, cycloheptyl propionate, cyclooctyl propionate, cyclopentyl butyrate, cyclohexyl butyrate, cycloheptyl butyrate, cyclooctyl butyrate, etc.; unsaturated aliphatic esters such as vinyl formate, allyl formate, methallyl formate, crotonyl formate, vinyl acetate, allyl acetate, methallyl acetate, crotonyl acetate, vinyl propionate, allyl propionate, methallyl propionate, crotonyl propionate, vinyl butyrate, allyl butyrate, methallyl butyrate, crotonyl butyrate, etc.; unsaturated esters such as methyl acrylate, methyl crotonate, methyl oleate, allyl acrylate, etc.; cycloalkenyl esters such as cyclopentenyl formate, cyclohexenyl formate, cycloheptenyl formate, cyclooctenyl formate, cyclopentenyl acetate, cyclohexenyl acetate, cycloheptenyl acetate, cyclooctenyl acetate, cyclopentenyl propionate, cyclohexenyl propionate, cycloheptenyl propionate, cyclooctenyl propionate, cyclopentenyl butyrate, cyclohexenyl butyrate, cycloheptenyl butyrate, cyclooctenyl butyrate, etc.; aryl esters such as benzyl formate, benzyl acetate, benzyl propionate, benzyl butyrate, benzyl benzoate, etc. It is to be understood that, as in the case of the acids, the esters herein listed are only representative of the class of esters which may be employed, and that the present invention is not necessarily limited thereto.

The esterification of the carboxylic acid is accomplished by reacting said acid with an ester in the presence of a catalytic amount, based on the carboxylic acid, of a tin halide. In the preferred embodiment of the invention the tin halide compound will comprise a halide of tin in its highest valence state, that is, stannic chloride, stannic bromide, stannic iodide, etc., the preferred catalyst due to its greater availability and greater activity comprising stannic chloride and preferably in an anhydrous form. It is also contemplated within the scope of this invention that hydrated forms of the stannic halide such as stannic chloride pentahydrate, stannic bromide pentahydrate, stannic iodide pentahydrate, may also be used although not necessarily with equivalent results. As was previously set forth, it was unexpected that an esterification of the carboxylic acid by treatment with an ester could be effected by utilizing only a catalytic amount of the tin halide rather than the stoichiometric amount based upon the carboxylic acid.

The process of this invention may be effected in any suitable manner and may comprise either a batch or continuous type operation. For example, when a batch type operation is used, a quantity of the reactants, namely, the carboxylic acid and the ester of the type hereinbefore set forth in greater detail are placed in an appropriate apparatus which may comprise a flask or, if superatmospheric pressures are to be employed, an autoclave of the rotating or mixing type. Following this, the catalytic amount of the tin halide is added at which time, due to the exothermic nature of the reaction, a rise in temperature will occur, or the ester may be gradually added to a stirred mixture of the acid and the catalyst. The temperature at which the reaction is effected may be controlled by external means, that is, either cooling means if it is desired to effect the reaction at room temperature or below, or conversely, heating means if temperatures ranging from about 50° to 100° C. are desired. The reaction is allowed to proceed for a predetermined period of time which may range from about 0.5 up to about 20 hours or more in duration, said residence time being dependent upon the various parameters of the reaction including temperature, pressure and type of reactants employed. In the event that superatmospheric pressures are employed, these pressures are afforded by introducing a substantially inert gas such as nitrogen into the reaction apparatus. Upon completion of the desired residence time, heating or cooling is discontinued and the apparatus and contents thereof are allowed to return to room temperature. The reaction mixture is then recovered and subjected to conventional means of separation such as fractional distillation whereby the desired products are recovered.

It is also contemplated within the scope of this invention that the process in which a carboxylic acid is treated with an ester may be effected in a continuous manner of operation. When such a type of operation is employed, the starting materials comprising the ester and the carboxylic acid are continuously charged to a reaction zone which is maintained at the proper operating conditions of temperature and pressure. In addition, the tin halide catalyst is also charged to the reactor through a separate line or, if so desired, it may be admixed with one or both of the reactants and the resulting mixture charged thereto in a single stream. Alternatively, the catalyst may be added to one of the reactants and the mixture charged through one line, the other reactant being charged through another line. Upon completion of the desired residence time, the reactor effluent is continuously withdrawn and subjected to conventional means of separation whereby the desired product is separated and recovered while any unreacted starting materials may be recycled to form a portion of the feed stock.

The following examples are given for purposes of illustrating the process of the present invention in which a carboxylic acid is esterified by treatment with an ester in the presence of certain catalytic compositions of matter. However, these examples are given merely for purposes of illustration and the present invention is not necessarily limited thereto.

EXAMPLE I

In this example 24 grams (0.24 mole) of allyl acetate, 54 grams (0.73 mole) of propionic acid and 20 grams (0.08 mole) of anhydrous stannic chloride were placed in the glass liner of a rotating autoclave. The autoclave was sealed and 30 atmospheres of nitrogen was pressed in. Thereafter the autoclave was heated to a temperature of 100° C. and maintained thereat for a period of 4 hours, while constantly rotating the autoclave. During this time the maximum pressure rose to 44 atmospheres. At the end of the 4-hour period, heating was discontinued and the autoclave was allowed to return to room temperature, the final pressure at room temperature being 30 atmospheres. Thereafter the excess pressure was discharged and the autoclave was opened. The reaction mixture was recovered and analyzed by means of gas-liquid chromatography which showed the presence of a major portion of allyl propionate.

EXAMPLE II

In a manner similar to that set forth in Example I above 39 grams (0.45 mole) of vinyl acetate (which was stabilized with hydroquinone) and 131 grams (1.77 mole) of propionic acid were placed in an Erlenmeyer flask provided with a magnetic bar for stirring the reactants. Thereafter, 9 grams (0.03 mole) of stannic chloride was added dropwise during a period of 5 minutes to the stirred mixture of the reactants. Due to the exothermicity of the reaction the temperature rose to 43° C. and was maintained thereat for a period of 2 hours while constantly stirring the product. At the end of this time the reaction product comprising vinyl propionate was recovered.

EXAMPLE III

To the glass liner of a rotating autoclave was added 37 grams (0.37 mole) of allyl acetate, 48 grams (0.29 mole) of phthalic acid and 9 grams (0.03 mole) of anhydrous stannic chloride. The autoclave was sealed and nitrogen pressed in until an initial operating pressure of 30 atmospheres was reached. Thereafter the autoclave was heated to a temperature of 100° C. and maintained in a range of from 99°-102° C. for a period of 4 hours, the maximum pressure at this temperature reaching 45 atmospheres. At the end of the 4-hour period, heating was discontinued and the autoclave was allowed to return to room temperature. After standing at room temperature for a period of 16 hours the excess pressure was discharged and the autoclave was opened. The desired product comprising allyl phthalate was recovered therefrom.

EXAMPLE IV

To the glass liner of a rotating autoclave may be added 42.4 grams (0.2 mole) of benzyl benzoate and 69 grams (0.8 mole) of crotonic acid along with 9 grams of stannic chloride pentahydrate. The autoclave may then be sealed and nitrogen pressed in until an initial operating pressure of 30 atmospheres is reached. Thereafter the autoclave and contents may be heated to a temperature of 100° C. and maintained at this temperature for a period of 4 hours, the autoclave and contents being constantly rotated during this residence time. At the end of the aforementioned time period, heating may be discontinued and after the autoclave has returned to room temperature the excess pressure may be discharged and the autoclave opened. The desired product comprising benzyl crotonate may then be recovered from the mixture.

EXAMPLE V

In a manner similar to that set forth in the above examples, 25.6 grams (0.2 mole) of butyl acrylate and 89.6 grams (0.7 mole) of cyclohexanecarboxylic acid along with 13 grams (0.03 mole) of stannic bromide may be placed in a glass liner of a rotating autoclave. Following this, the autoclave may be sealed and nitrogen pressed in until an initial operating pressure of 30 atmospheres is reached. The autoclave may then be heated to a temperature of 100° C. and maintained in a range of from about 100°-102° C. for a period of 4 hours. At the end of this 4-hour period, heating is discontinued and the autoclave is allowed to return to room temperature. After allowing the autoclave to stand for a period of 16 hours, the excess pressure may be discharged and the autoclave opened. The desired product comprising butyl cyclohexanecarboxylate may then be recovered from the mixture.

I claim as my invention:

1. A transesterification process which comprises reacting, in the presence of a catalytic amount of stannic chloride, bromide or iodide at a temperature in the range of from about 0° to about 150° C. and a pressure in the range of from about atmospheric to about 100 atmospheres, a carboxylic acid selected from the group consisting of fatty acids of from 1 to about 20 carbon atoms, cycloalkanecarboxylic acids having from 5 to 8 carbon atoms in the ring and aromatic carboxylic acids with an alkyl, cycloalkyl, unsaturated aliphatic, cycloaliphatic or benzyl formate, acetate, butyrate, acrylate, crotonate, oleate or benzoate, and recovering the resultant esterified carboxylic acid.

2. The process as set forth in claim 1 in which the catalyst is anhydrous stannic chloride.

3. The process as set forth in claim 1 in which the catalyst is stannic chloride pentahydrate.

4. The process as set forth in claim 1 in which the catalyst is stannic bromide.

5. The process as set forth in claim 1 in which said acid is propionic acid, said ester is allyl acetate and said esterified carboxylic acid is allyl propionate.

6. The process as set forth in claim 1 in which said acid is propionic acid, said ester is vinyl acetate and said esterified carboxylic acid is vinyl propionate.

7. The process as set forth in claim 1 in which said acid is phthalic acid, said ester is allyl acetate and said esterified carboxylic acid is allyl phthalate.

8. The process as set forth in claim 1 in which said acid is crotonic acid, said ester is benzyl benzoate and said esterified carboxylic acid is benzyl crotonate.

9. The process as set forth in claim 1 in which said acid is cyclohexanecarboxylic acid, said ester is butyl acrylate and said esterified carboxylic acid is butyl cyclohexanecarboxylate.

* * * * *